United States Patent

Kelly

[11] 3,974,173
[45] Aug. 10, 1976

[54] OXAZOLIDINES OF ENDO-6-FORMYL-EXO-3-HYDROXYBICYCLO[3.1.0]HEXAN-EXO-2-ACETIC ACID, δ-LACTONE

[75] Inventor: Robert C. Kelly, Kalamazoo, Mich.

[73] Assignee: The Upjohn Company, Kalamazoo, Mich.

[22] Filed: Apr. 23, 1975

[21] Appl. No.: 570,670

Related U.S. Application Data

[60] Continuation-in-part of Ser. No. 315,365, Dec. 15, 1972, abandoned, which is a division of Ser. No. 181,246, Sept. 16, 1971, Pat. No. 3,711,515, which is a continuation-in-part of Ser. No. 93,483, Nov. 27, 1970, abandoned.

[52] U.S. Cl..................... 260/307 FA; 260/343.3 R
[51] Int. Cl.² ........................................ C07D 263/06
[58] Field of Search................................ 260/307 FA

[56] References Cited
UNITED STATES PATENTS
3,711,515  1/1973  Kelly.............................. 260/343.3

Primary Examiner—Nicholas S. Rizzo
Assistant Examiner—Mary C. Vaughn
Attorney, Agent, or Firm—Morris L. Nielsen

[57] ABSTRACT

Oxazolidines having the formula

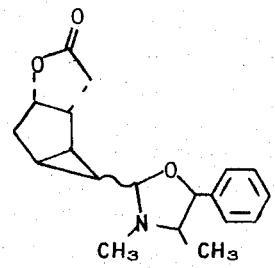

wherein ~ indicates endo or exo attachment, but differing in their stereoisomeric configuration, are prepared by reaction of the isomers of a tricyclic lactone aldehyde of the formula

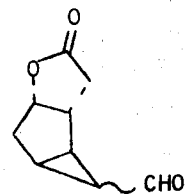

wherein ~ is as defined above, with d- or l-ephedrine; useful for separating optically active isomers of the aldehyde.

2 Claims, 1 Drawing Figure

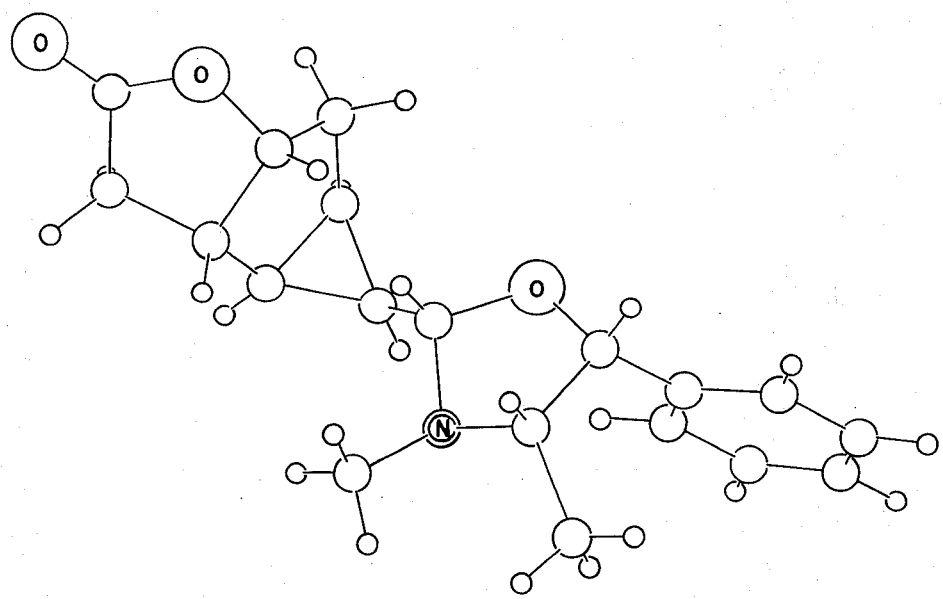

OXAZOLIDINES OF ENDO-6-FORMYL-EXO-3-HYDROXYBICY-CLO[3.1.0]HEXAN-EXO-2-ACETIC ACID, δ-LACTONE

CROSS REFERENCE TO RELATED APPLICATIONS

This application is a continuation-in-part of my copending application Ser. No. 315,365, filed Dec. 15, 1972, now abandoned which was a divisional application of then copending application Ser. No. 181,246, filed Sept. 16, 1971 and now issued as U.S. Pat. No. 3,711,515, which was a continuation-in-part of then copending application Ser. No. 93,483, filed Nov. 27, 1970, and since abandoned.

BACKGROUND OF THE INVENTION

This invention relates to intermediates useful in the preparation of prostaglandins (hereinafter identified as "PGF$_{2\alpha}$ ", etc.) More particularly, the invention relates to oxazolidines which are useful for the separation of optical isomers of said intermediates.

SUMMARY OF THE INVENTION

This invention provides novel oxazolidines which are obtained from isomers of tricyclic lactone aldehydes of the formula

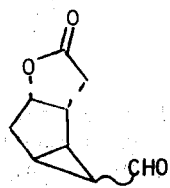

wherein ~ indicates endo or exo attachment. Said aldehydes are described in U.S. Pat. No. 3,816,462, issued June 11, 1974, to Robert C. Kelly, which was a divisional application of Ser. No. 181,246, filed Sept. 16, 1971, identified above as a parent of the instant application. All relevant subject matter in said U.S. Pat. No. 3,816,462 is incorporated herein by reference, particularly as relating to the preparation, properties and uses of the above-identified tricyclic lactone aldehydes and their oxazolidines.

In conformance with the requirements of the Manual of Patent Examining Procedure Sec. 608.01(p) on Incorporation by Reference, an abstract of that patent is reproduced as follows:

Process for preparing an optically active tricyclic lactone aldehyde of the formula

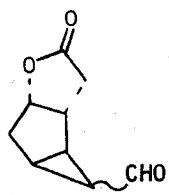

or the mirror image thereof, or a racemic compound of that formula and the mirror image thereof, wherein ~ indicates attachment of the moiety to the cyclopropane ring in exo or endo configuration. The tricyclic lactone aldehydes are useful intermediates in preparing prostaglandins having pharmacological utility.

A brief summary of that invention is: to provide processes for the production of compounds useful in the preparation of prostaglandins commercially in substantial amount and at reasonable cost; to provide intermediates useful in such processes. There was no drawing in that patent. Claim 1 from that patent is as follows:

1. An optically active compound of the formula

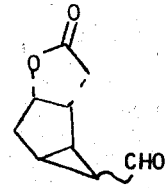

or the mirror image thereof, or a racemic compound of that formula and the mirror image thereof, wherein ~ indicates attachment of the moiety to the cyclopropane ring in exo or endo configuration.

As further disclosed in said referenced patent particularly in columns 17, 26, and 27, one method of resolving a racemic mixture of aldehyde I and separating the optical isomers of aldehydes represented by formula I and its mirror image consists of preparing oxazolidines by reaction of the racemic aldehyde with d- or l-ephedrine, separating said diastereomeric oxazolidines, and hydrolyzing the oxazolidines to the respective optically active aldehydes.

It is a purpose of this invention to identify and claim the oxazolidines as novel compounds.

EXAMPLE 1 (based on Example 11 of referenced U.S. Pat. No. 3,816,462)

A. A solution of endo formula I dl-lactone aldehyde (0.5 g.) and l-ephedrine (0.5 g.) in benzene (20 ml.) is concentrated under vacuum to a residue. The residue is treated with diethyl ether to yield crystals of an oxazolidine mixture. Recrystallization of the mixture from methanol yields an oxazolidine "EL", M.P. 133.5–134.5° C. Hydrolysis of this ozazolidine yields the enantiomeric formula I lactone aldehyde, i.e. the optically active isomer represented by the mirror image of the formula I aldehyde as drawn.

Selected crystals of the oxazolidine grown from methanol solution are subjected to X-ray crystallographic analysis and the oxazolidine is thereby identified as (1R, 2S, 2'S, 3R, 4'S, 5R, 5'R, 6R)-3-hydroxy-6-(3',4'-dimethyl-5'-phenyl-2'-oxazolidinyl)bicyclo[3.1.0]hexane-2-acetic acid, γ-lactone, represented by the formula:

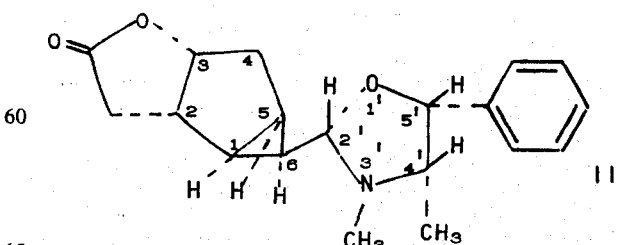

A drawing of the crystal structure as obtained from 3-dimensional coordinates through a computer plotter is attached as the FIGURE.

Oxazolidine "EL" (1.0 g.) is dissolved in a few ml. of dichloromethane, charged to a 20 g. silica gel column and eluted with dichloromethane. The silica gel is chromatography-grade (Merck), 0.05–0.1 mm. particle size, with about 4–5 g. water per 100 g. Those fractions of eluate which are shown by thin layer chromatography to contain the aldehyde are combined and concentrated to yield the separated isomer, in this instance the optically active enantiomer of the formula I lactone aldehyde as represented by the mirror image of formula I wherein ~ is endo, and identified hereinafter as the "isomer of Example 1-A."

B. Following the procedure of Example 1-A, but replacing l-ephedrine with d-ephedrine in preparing the oxazolidine, there is obtained an oxazolidine "ND" as crystals from the mixture. This oxazolidine is identified as (1S, 2R, 2'R, 3S, 4'R, 5S, 5'S, 6S)-3-hydroxy-6-(3',-4'-dimethyl-5'-phenyl-2'-oxazolidinyl)bicyclo[3.1.0-]hexane-2-acetic acid, γ-lactone, represented by the formula:

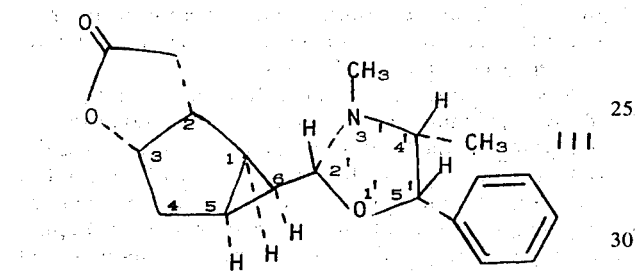

III

Thereafter, the oxazolidine is hydrolyzed following the procedure of Example 1-A but yielding the optically active formula I aldehyde, hereinafter identified as the "isomer of Example 1-B".

C. The mother liquor from part A is concentrated and chilled to yield another diastereomeric oxazolidine "NL". This same oxazolidine is prepared in pure form from the reaction of the aldehyde isomer of Example 1-B with l-ephedrine following the procedure of Example 1-A. This oxazolidine is identified as (1S, 2R, 2'S, 3S, 4'S, 5S, 5'R, 6S)-3-hydroxy-6-(3',4'-dimethyl-5'-phenyl-2'-oxazolidinyl)bicyclo[3.1.0]hexane-2-acetic acid, γ-lactone, represented by the formula:

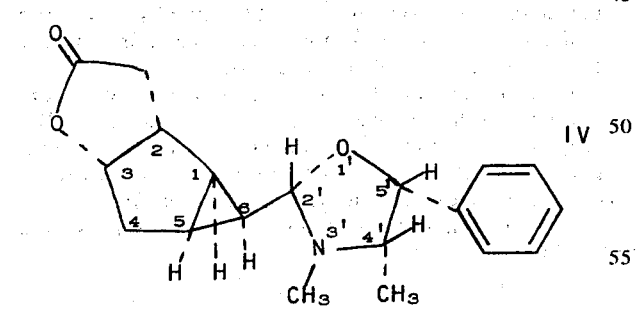

IV

Upon hydrolysis, oxazolidine "NL" yields the aldehyde isomer of Example 1-B.

D. The mother liquor from part B is concentrated and chilled to yield oxazolidine "ED". This same oxazolidine is prepared in pure form from the reaction of the aldehyde isomer of Example 1-A with d-ephedrine following the procedure of Example 1-A. This oxazolidine is identified as (1R, 2S, 2'R, 3R, 4'R, 5R, 5'S, 6R)-3-hydroxy-6-(3',4'-dimethyl-5'-phenyl-2'-oxazolidinyl)bicyclo[3.1.0]hexane-2-acetic acid, γ-lactone, represented by formula:

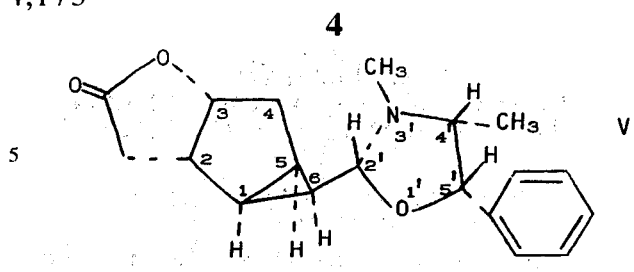

V

Following the procedures of Example 1, the exo formula I dl-lactone aldehyde is transformed into the respective oxazolidines and thereafter into the separate optically active isomers corresponding to the formula I aldehyde wherein ~ is exo.

The oxazolidines are as follows:

(1R, 2S, 2'R, 3R, 4'S, 5R, 5'R, 6S)-3-hydroxy-6-(3',-4'-dimethyl-5'-phenyl-2'-oxazolidinyl)bicyclo[3.1.0-]hexane-2-acetic acid, γ-lactone, represented by formula:

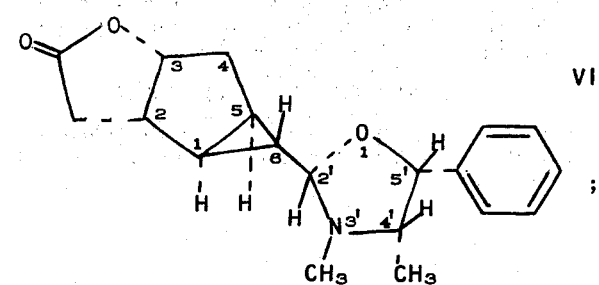

VI (1S, 2R, 2'S, 3S, 4'R, 5S, 5'S 6R)-3-hydroxy-6-(3',4'-dimethyl-5'-phenyl-2'-oxazolidinyl)bicyclo[3.1.0]hexane-2-acetic acid, γ-lactone, represented by formula:

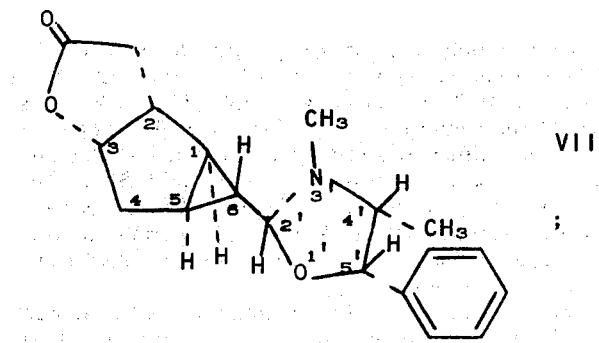

VII (1S, 2R, 2'R, 3S, 4'S, 5S, 5'R, 6R)-3-hydroxy-6-(3', 4'-dimethyl-5'-phenyl-2'-oxazolidinyl)bicyclo[3.1.0-]hexane-2-acetic acid,γ-lactone, represented by formula:

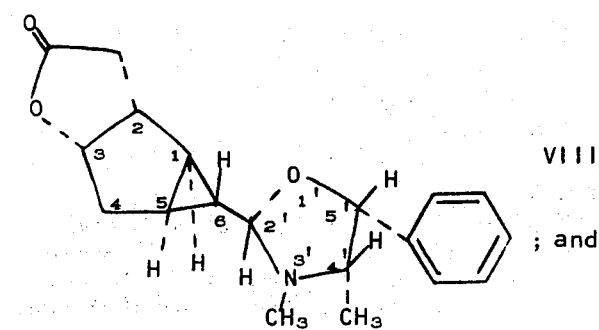

VIII

; and (1R, 2S, 2′S, 3R, 4′R, 5R, 5′S, 6S)-3-hydroxy-6-(3′,4′-dimethyl-5′-phenyl-2′-oxazolidinyl)bicyclo[3.1.0]hexane-2-acetic acid, γ-lactone, represented by formula:

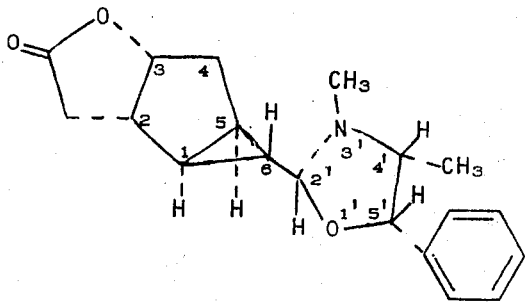

IX

Thereafter, each of the oxazolidines V-IX is hydrolyzed to the respective endo or exo optically active isomer corresponding to the formula 1 tricyclic lactone aldehyde, each of which is a useful intermediate for preparing prostaglandins or prostaglandin analogs.

I claim:
1. An oxazolidine, which is (1R, 2S, 2′S, 3R, 4′S, 5R, 5′R, 6R)-3-hydroxy-6-(3′,4′-dimethyl-5′-phenyl-2′-oxazolidinyl)bicyclo[3.1.0]hexane-2-acetic acid, γ-lactone, represented by formula II.
2. An oxazolidine, which is (2S, 2R, 2′R, 3S, 4′R, 5S, 5′S, 6S)-3-hydroxy-6-(3′,4′-dimethyl-5′-phenyl-2′-oxazolidinyl)bicyclo[3.1.0]hexane-2-acetic acid, γ-lactone, represented by formula III.

* * * * *

UNITED STATES PATENT AND TRADEMARK OFFICE
CERTIFICATE OF CORRECTION

PATENT NO. : 3,974,173
DATED : August 10, 1976
INVENTOR(S) : Robert C. Kelly

It is certified that error appears in the above-identified patent and that said Letters Patent are hereby corrected as shown below:

Column 6, line 11 "(2S," should read -- (1S, --.

Signed and Sealed this

Second Day of November 1976

[SEAL]

Attest:

RUTH C. MASON
*Attesting Officer*

C. MARSHALL DANN
*Commissioner of Patents and Trademarks*